US006924135B2

(12) United States Patent
Lillehoj et al.

(10) Patent No.: US 6,924,135 B2
(45) Date of Patent: Aug. 2, 2005

(54) DNA ENCODING EIMERIA GLYCEROALDEHYDE-3-PHOSPHATE DEHYDROGENASE AND USES THEREOF

(75) Inventors: Hyun Lillehoj, West Friendship, MD (US); Wongi Min, Greenbelt, MD (US); Takanori Sato, Tokyo (JP); Atsushi Yasuda, Tokyo (JP)

(73) Assignee: Zeon Corporation, Tokyo (JP)

( * ) Notice: Subject to any disclaimer, the term of this patent is extended or adjusted under 35 U.S.C. 154(b) by 151 days.

(21) Appl. No.: 10/651,013

(22) Filed: Aug. 29, 2003

(65) Prior Publication Data

US 2005/0048632 A1 Mar. 3, 2005

(51) Int. Cl.[7] .......................... C12N 15/00; C12N 9/04; A61K 38/44; A01N 63/00; C07H 21/04

(52) U.S. Cl. ................. 435/190; 435/320.1; 435/252.3; 435/4; 435/6; 435/69.1; 435/183; 424/93.1; 424/94.4; 536/23.2; 536/23.4; 536/23.7

(58) Field of Search ............................. 435/190, 252.3, 435/320.1; 424/93.1, 94.4; 536/23.2

(56) References Cited

U.S. PATENT DOCUMENTS

| | | | | |
|---|---|---|---|---|
| 5,028,694 | A | 7/1991 | Mewman, Jr. et al. | 530/350 |
| 5,122,471 | A | 6/1992 | Jenkins et al. | 435/252.3 |
| 5,279,960 | A | 1/1994 | Anderson et al. | 435/243 |
| 5,387,414 | A | 2/1995 | Harwood et al. | 424/191.1 |
| 5,403,581 | A | 4/1995 | Binger et al. | 424/191.1 |
| 5,449,768 | A | 9/1995 | Chakraborty et al. | 536/24.32 |
| 5,602,033 | A | 2/1997 | Vermeulen et al. | 435/252.33 |
| 5,814,320 | A | 9/1998 | Clarke et al. | 424/267.1 |
| 6,001,363 | A | 12/1999 | Tomley et al. | 424/191.1 |

FOREIGN PATENT DOCUMENTS

WO WO 99/18215 4/1999

OTHER PUBLICATIONS

L. Argiro et al.; "Identification of a candidate vaccine peptide on the 37 kDa *Shistosoma mansoni* GAPDH"; Vaccine 18 (2000), 2039–2040.

L. Argiro et al.; "Induction of a protective immunity against *Schistosoma mansoni* with ovalbumin–coupled Sm37–5 coadsorbed with granulocyte–macrophage colony stimulating factor(GM–CSF) or IL–12 on alum"; Vaccine 17 (1999) 13–18.

M. Jenkins et al.; "Eimeria acervuline: DNA Cloning and Characterization of Recombinant Sporozoite and Merozoite Antigens"; Experimental Parasitology 66, 96–107 (1998).

G. Waine et al.; "Cloning, Molecular Characterization, and Functional Activity of *Schistosoma japonicum* Glyceraldehyde–3–Phosphate Dehydrogenase, a Putative Vaccine Candidate against Schistosomiasis Japonica", Infection and Immunity, Nov. 1993, 4716–4723.

A. Pitarch et al.; "Two–dimensional gel electrophoresis as analytical tool for identifying *Candida albicans* immunogenic proteins", Electrophoresis 1999, 20, 1001–1010.

N. Balaban et al.; "Intracellular Antigens (Microtubule–Associated Protein Copurified with Glycosomal Enzymes)—Possible Vaccines against Trypanosomiasis", Journal of Infectious Disease, 1995; 172 (Sep.), 845–850.

(Continued)

*Primary Examiner*—Marijunath Rao
*Assistant Examiner*—Yong Pak
(74) *Attorney, Agent, or Firm*—Armstrong, Kratz, Quintos, Hanson & Brooks, LLP

(57) ABSTRACT

This invention relates to a novel DNA encoding *Eimeria* glyceroaldehyde-3-phosphate dehydrogenase (GAPDH) and recombinant GAPDH protein expressed using the DNA sequence. The present invention further provides the recombinant vector or virus containing this DNA. The chickens immunized by the recombinant virus or recombinant GAPDH protein described herein can be induced immunity against coccidiosis.

6 Claims, 5 Drawing Sheets

OTHER PUBLICATIONS

Figure 1:
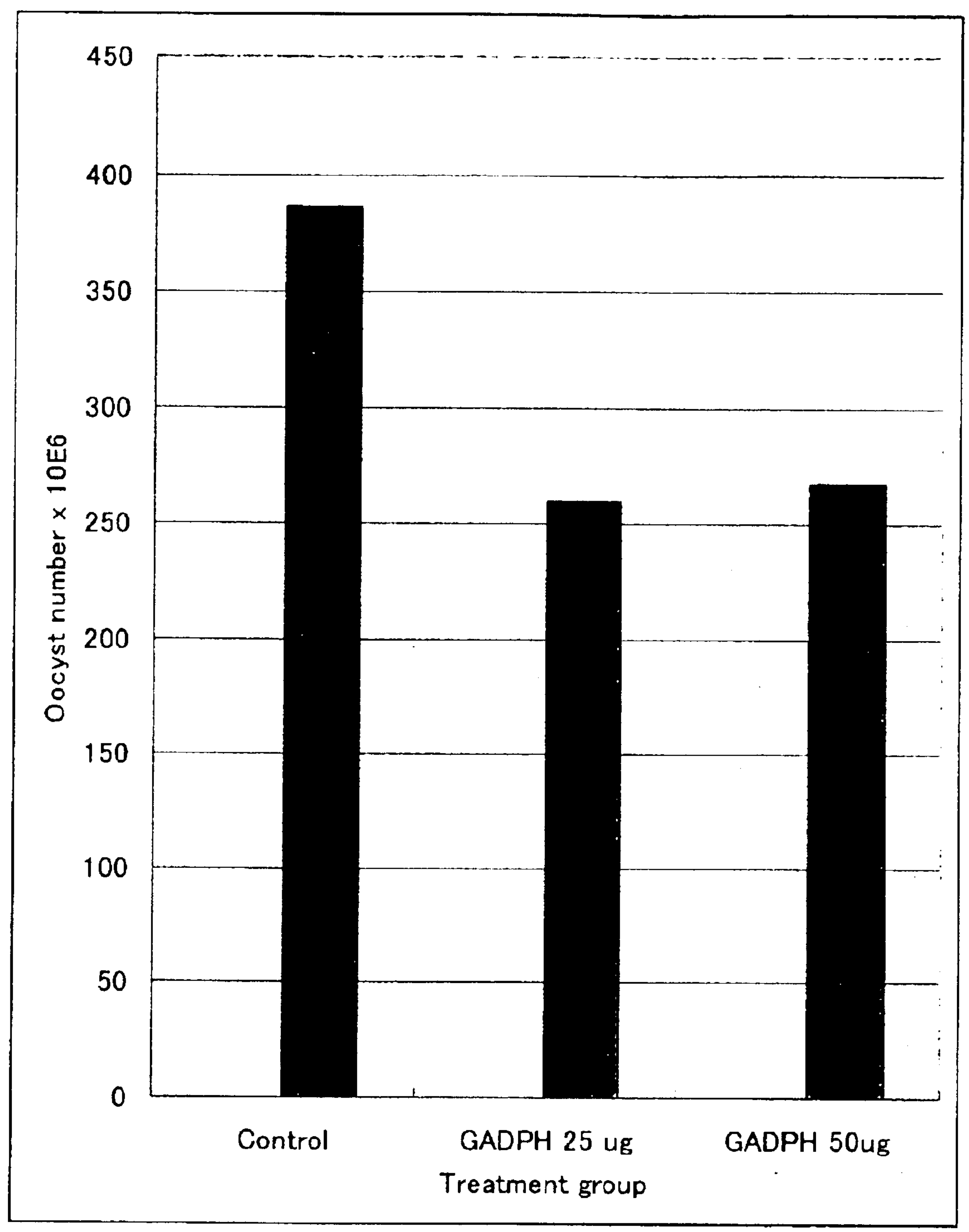

G. Rosinha et al.; "Molecular and immunological characterization of recombinant *Brucella abortus* glyceraldehyde–3–phosphate–dehydrogenate, a T– and B–cell reactive protein that induces partial protection when co–administered with an interleukin–12–expressing plasmid in a DNA vaccine formulation"; J. Med. Microbiol, vol. 51, (2002), 661–671.

A. Davidson et al.; "Structure of Vaccinia Virus Early Promotors", J. Mol. Biol., (1989), 210, 749–769.

A Davidson et al.; "Structure of Vaccinia Virus Late Promotors", J. Mol. Biol., (1989), 210, 771–784.

T. Jeffers; "Attenuation of *Eimeria Tenella* through selection for precociousness", J. of Parasitology, vol. 61, No. 6, Dec. 1975, 1083–1090.

R. Witter et al.; "Isolation of Turkeys of a Cell–Associated Herpesvirus Antigenically Related to Marek's Disease Virus", Am. J. Vet. Res., vol. 31, No. 3, Mar. 1970, 525–538.

SEQUENCE LISTING

```
<160> NUMBER OF SEQ ID NOS: 14

<210> SEQ ID NO 1
<211> LENGTH: 1280
<212> TYPE: DNA
<213> ORGANISM: Eimeria spp.
<220> FEATURE:
<221> NAME/KEY: CDS
<222> LOCATION: (59)..(1078)

<400> SEQUENCE: 1

ctctgcacac tgaggcgctt ttctttagtt ttgcacagca tatccttact cagcgaaa       58

atg gtg tgc cgt atg gga atc aac ggc ttc ggc cgc atc ggc cgt ttg      106
Met Val Cys Arg Met Gly Ile Asn Gly Phe Gly Arg Ile Gly Arg Leu
  1               5                  10                  15

gtc ttc cgc gcc gct atg gcc aac cct gaa gtg gaa gtc gtc gca gtg      154
Val Phe Arg Ala Ala Met Ala Asn Pro Glu Val Glu Val Val Ala Val
             20                  25                  30

aac gac ccg ttc atg gac gtg cag tac atg gcc tac cag ctg aag tac      202
Asn Asp Pro Phe Met Asp Val Gln Tyr Met Ala Tyr Gln Leu Lys Tyr
         35                  40                  45

gac tct gtg cac ggc aaa ttc cct gga gaa gtg agc gtg aag gac ggc      250
Asp Ser Val His Gly Lys Phe Pro Gly Glu Val Ser Val Lys Asp Gly
     50                  55                  60

aat ttg gta gtg gag ggg aag aca atc caa gtg ttt gct gag aag gac      298
Asn Leu Val Val Glu Gly Lys Thr Ile Gln Val Phe Ala Glu Lys Asp
 65                  70                  75                  80

ccc gca gcc att cct tgg ggc aag gtt ggt gct cac tac gtg tgc gag      346
Pro Ala Ala Ile Pro Trp Gly Lys Val Gly Ala His Tyr Val Cys Glu
                 85                  90                  95

tca act ggt gta ttc aca aac aag gag aag gct ggt ctg cac ata tct      394
Ser Thr Gly Val Phe Thr Asn Lys Glu Lys Ala Gly Leu His Ile Ser
            100                 105                 110

ggc ggt gct aag aag gtc att atc tct gct cct cct aag gat gac acc      442
Gly Gly Ala Lys Lys Val Ile Ile Ser Ala Pro Pro Lys Asp Asp Thr
        115                 120                 125

ccc atg ttc gtt atg ggt gtg aac cac gag gaa tac cag ccc act ctt      490
Pro Met Phe Val Met Gly Val Asn His Glu Glu Tyr Gln Pro Thr Leu
    130                 135                 140

cag gtt gtt tct aat gct tcc tgc act acc aac tgc ctc gct cct ctt      538
Gln Val Val Ser Asn Ala Ser Cys Thr Thr Asn Cys Leu Ala Pro Leu
145                 150                 155                 160

gcg aag gtg gtg cac gag aag ttc ggt att gtt gag ggt ctt atg acc      586
Ala Lys Val Val His Glu Lys Phe Gly Ile Val Glu Gly Leu Met Thr
                165                 170                 175

acc gtg cac gct atg aca gct aac cag ctg act gtt gat ggc cca tca      634
Thr Val His Ala Met Thr Ala Asn Gln Leu Thr Val Asp Gly Pro Ser
            180                 185                 190

aag gga ggg aag gac tgg agg gct gga cgc tgt gca ggc agc aac att      682
Lys Gly Gly Lys Asp Trp Arg Ala Gly Arg Cys Ala Gly Ser Asn Ile
        195                 200                 205

atc cct gca agc aca ggt gca gca aag gca gta ggg aaa gtt att cct      730
Ile Pro Ala Ser Thr Gly Ala Ala Lys Ala Val Gly Lys Val Ile Pro
    210                 215                 220

tct ctt aac ggc aag ctt aca ggc atg gct ttc cgt gtg ccc acc cct      778
Ser Leu Asn Gly Lys Leu Thr Gly Met Ala Phe Arg Val Pro Thr Pro
225                 230                 235                 240

gac gtc tcc gtc gtc gac ctc aca tgc agg ctg tct aag ccc gcc aag      826
Asp Val Ser Val Val Asp Leu Thr Cys Arg Leu Ser Lys Pro Ala Lys
```

-continued

```
              245                 250                 255

tac gaa gac att gtc gct gcc atc cgt gca gct tct gag ggc ccc ctt      874
Tyr Glu Asp Ile Val Ala Ala Ile Arg Ala Ala Ser Glu Gly Pro Leu
            260                 265                 270

aag ggt att ttg ggt gtc aca gag gag gag gtt gta tcc cag gac ttc      922
Lys Gly Ile Leu Gly Val Thr Glu Glu Glu Val Val Ser Gln Asp Phe
        275                 280                 285

tgt ggt gat aag aga tcc tct atc ttc gac gtc aag gca ggt att cag      970
Cys Gly Asp Lys Arg Ser Ser Ile Phe Asp Val Lys Ala Gly Ile Gln
    290                 295                 300

ctt aac gac tcc ttc gtt aag ctc gtc tcc tgg tat gac aac gag tgg     1018
Leu Asn Asp Ser Phe Val Lys Leu Val Ser Trp Tyr Asp Asn Glu Trp
305                 310                 315                 320

gga tac tct aac aga ctt gta gat ctt gca atc tac atg tct aag aag     1066
Gly Tyr Ser Asn Arg Leu Val Asp Leu Ala Ile Tyr Met Ser Lys Lys
              325                 330                 335

gac ggc aac taa aacaaaggag cgtatgaaca acccctttct gtcgccttat         1118
Asp Gly Asn

tttagtacac tttagtattt gtgcattgtt ctcctcgggg gacagaataa ggggtaggct   1178

gtggcgccac ctatcaaaac agacccaaat atttcttgca gaagggcagc ccctgtccga   1238

aacaacccac aatcaatttt cctgtgtaaa aaaaaaaaaa aa                      1280


<210> SEQ ID NO 2
<211> LENGTH: 339
<212> TYPE: PRT
<213> ORGANISM: Eimeria spp.

<400> SEQUENCE: 2

Met Val Cys Arg Met Gly Ile Asn Gly Phe Gly Arg Ile Gly Arg Leu
  1               5                  10                  15

Val Phe Arg Ala Ala Met Ala Asn Pro Glu Val Glu Val Val Ala Val
            20                  25                  30

Asn Asp Pro Phe Met Asp Val Gln Tyr Met Ala Tyr Gln Leu Lys Tyr
        35                  40                  45

Asp Ser Val His Gly Lys Phe Pro Gly Glu Val Ser Val Lys Asp Gly
    50                  55                  60

Asn Leu Val Val Glu Gly Lys Thr Ile Gln Val Phe Ala Glu Lys Asp
 65                  70                  75                  80

Pro Ala Ala Ile Pro Trp Gly Lys Val Gly Ala His Tyr Val Cys Glu
                 85                  90                  95

Ser Thr Gly Val Phe Thr Asn Lys Glu Lys Ala Gly Leu His Ile Ser
            100                 105                 110

Gly Gly Ala Lys Lys Val Ile Ile Ser Ala Pro Pro Lys Asp Asp Thr
        115                 120                 125

Pro Met Phe Val Met Gly Val Asn His Glu Glu Tyr Gln Pro Thr Leu
    130                 135                 140

Gln Val Val Ser Asn Ala Ser Cys Thr Thr Asn Cys Leu Ala Pro Leu
145                 150                 155                 160

Ala Lys Val Val His Glu Lys Phe Gly Ile Val Glu Gly Leu Met Thr
                165                 170                 175

Thr Val His Ala Met Thr Ala Asn Gln Leu Thr Val Asp Gly Pro Ser
            180                 185                 190

Lys Gly Gly Lys Asp Trp Arg Ala Gly Arg Cys Ala Gly Ser Asn Ile
        195                 200                 205

Ile Pro Ala Ser Thr Gly Ala Ala Lys Ala Val Gly Lys Val Ile Pro
```

-continued

```
    210                 215                 220

Ser Leu Asn Gly Lys Leu Thr Gly Met Ala Phe Arg Val Pro Thr Pro
225                 230                 235                 240

Asp Val Ser Val Val Asp Leu Thr Cys Arg Leu Ser Lys Pro Ala Lys
                245                 250                 255

Tyr Glu Asp Ile Val Ala Ala Ile Arg Ala Ala Ser Glu Gly Pro Leu
            260                 265                 270

Lys Gly Ile Leu Gly Val Thr Glu Glu Glu Val Val Ser Gln Asp Phe
        275                 280                 285

Cys Gly Asp Lys Arg Ser Ser Ile Phe Asp Val Lys Ala Gly Ile Gln
    290                 295                 300

Leu Asn Asp Ser Phe Val Lys Leu Val Ser Trp Tyr Asp Asn Glu Trp
305                 310                 315                 320

Gly Tyr Ser Asn Arg Leu Val Asp Leu Ala Ile Tyr Met Ser Lys Lys
                325                 330                 335

Asp Gly Asn


<210> SEQ ID NO 3
<211> LENGTH: 1525
<212> TYPE: DNA
<213> ORGANISM: Gallus gallus
<220> FEATURE:
<221> NAME/KEY: promoter
<222> LOCATION: (21)..(1505)

<400> SEQUENCE: 3

ctgcagctca gtgcatgcac gctcattgcc catcgctatc cctgcctctc ctgctggcgc     60

tccccgggag gtgacttcaa ggggaccgca ggaccacctc gggggtgggg ggagggctgc    120

acacgcggac ccgctccccc ctccccaaca aagcactgtg gaatcaaaaa ggggggaggg    180

gggatggagg ggcgcgtcac acccccgccc cacaccctca cctcgaggtg agccccacgt    240

tctgcttcac tctccccatc tcccccccct ccccaccccc aattttgtat ttatttattt    300

tttaattatt ttgtgcagcg atgggggcgg gggggggggg ggcgcgcgcc aggcggggcg    360

gggcggggcc aggggcgggg cggggcgagg cggagaggtg cggcggcagc caatcagagc    420

ggcgcgctcc gaaagtttcc ttttatggcg aggcggcggc ggcggcggcc ctataaaaag    480

cgaagcgcgc ggcgggcggg agtcgctgcg cgctgccttc gccccgtgcc ccgctccgcc    540

gccgcctcgc gccgcccgcc ccggctctga ctgaccgcgt tactcccaca ggtgagcggg    600

cgggacggcc cttctcctcc gggctgtaat tagcgcttgg tttaatgacg gctcgtttct    660

tttctgtggc tgcgtgaaag ccttaaaggg ctccgggagg gccctttgtg cggggggggag   720

cggctcgggg ggtgcgtgcg tgtgtgtgtg cgtggggagc gccgcgtgcg gctccgcgct    780

gcccggcggc tgtgagcgct gcgggcgcgg cgcggggctt tgtgcgctcc gcagtgtgcg    840

cgaggggagc gcggccgggg gcggtgcccc gcggtgcggg gggggctgcg aggggaacaa    900

aggctgcgtg cggggtgtgt gcgtgggggg gtgagcaggg ggtgtgggcg cggcggtcgg    960

gctgtaaccc ccccctgcac ccccctcccc gaagttgctg agcacggccc ggcttcgggt   1020

gcggggctcc gtgcggggcg tggcgcgggg ctcgccgtgc cgggcggggg gtggcggcag   1080

gtgggggtgc cgggcggggc ggggccgcct cgggccgggg agggctcggg ggaggggcgc   1140

ggcggccccc ggagcgccgg cggctgtcga ggcgcggcga gccgcagcca ttgcctttta   1200

tggtaatcgt gcgagagggc gcagggactt cctttgtccc aaatctgtgc ggagccgaaa   1260

tctgggaggc gccgccgcac cccctctagc gggcgcgggg cgaagcggtg cggcgccggc   1320
```

aggaaggaaa tgggcgggga gggccttcgt gcgtcgccgc gccgccgtcc ccttctccat 1380
ctccagcctc ggggctgtcc gcagggggac ggctgccttc ggggggggacg gggcagggcg 1440 gggttcggct tctggcgtgt gaccggcggg gtttatatct tcccttctct gttcctccgc 1500
agcccccaag cttgtcgact ctaga 1525

<210> SEQ ID NO 4
<211> LENGTH: 39
<212> TYPE: DNA
<213> ORGANISM: Gallus gallus
<220> FEATURE:
<221> NAME/KEY: misc_feature
<222> LOCATION: (1)..(14)
<223> OTHER INFORMATION: Artificial sequence

<400> SEQUENCE: 4
cagtgtcgct gcagctcagt gcatgcacgc tcattgccc 39

<210> SEQ ID NO 5
<211> LENGTH: 49
<212> TYPE: DNA
<213> ORGANISM: Gallus gallus
<220> FEATURE:
<221> NAME/KEY: misc_feature
<222> LOCATION: (1)..(14)
<223> OTHER INFORMATION: Artificial sequence

<400> SEQUENCE: 5
gctctagagt cgacaagctt gggggctgcg gaggaacaga gaagggaag 49

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
gatcccctcg aggggggggcc 20

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
ccccctcgag gg 12

<210> SEQ ID NO 8
<211> LENGTH: 28
<212> TYPE: DNA
<213> ORGANISM: Simian virus 40
<220> FEATURE:
<221> NAME/KEY: misc_feature
<222> LOCATION: (1)..(8)
<223> OTHER INFORMATION: Artificial sequence

<400> SEQUENCE: 8
gcgggcccta attgtttgtg tattttag 28

<210> SEQ ID NO 9

-continued

<211> LENGTH: 29
<212> TYPE: DNA
<213> ORGANISM: Simian virus 40
<220> FEATURE:
<221> NAME/KEY: misc_feature
<222> LOCATION: (1)..(8)
<223> OTHER INFORMATION: Artificial sequence

<400> SEQUENCE: 9
ttggtaccgc ttacaattta cgcgttaag 29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: PCR primer

<400> SEQUENCE: 10
ccttactcag tctagaaaat ggtgtgccg 29

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 11
ctaaagtgta ctcgagtaag gcgacag 27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 12
gtgccgtatg ggatccaacg gcttcgg 27

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 13
ctaaagtgta ctcgagtaag gcgacag 27

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
Oligonucleotide

<400> SEQUENCE: 14
tccatgacgt tcctgacgtt 20

DNA ENCODING EIMERIA GLYCEROALDEHYDE-3-PHOSPHATE DEHYDROGENASE AND USES THEREOF

BACKGROUND OF THE INVENTION

1. Field of the Invention

Coccidiosis is an intestinal disorder of poultry and causes an assortment of problems in the infected host. These problems range from poor feed conversion ratios in light infections to acute death in heavier infections.

Coccidiosis is caused by protozoans belonging to the genus *Eimeria*. The members of this genus in poultry are *E. acervulina, E. tenella, E. maxima, E. necatrix, E. brunetti, E. mitis* and *E. praecox*. Some investigators include *E. mivati* and *E. hagani* into the member. All of these species have similar life cycles but display different tissue specificity and pathogenicity. A broiler chicken will be subjected to a great deal of damage by *E. acervulina* or *E. maxima* because they parasitize large portions of the small intestine, where food digestion plays a major role.

Coccidiosis can be controlled by the administration of anti-coccidial agents. However, drug resistant strains arise at a frequent rate and the cost of development of new drugs is quite high. In addition, a number of these agents leave residues in the meat, which might give problems on consumer.

Attempts have been made to prevent the disease by vaccinating chickens with live attenuated strains of *Eimeria* or inactivated parasites. These live attenuated strains such as precocious lines are obtained by inoculating chickens with oocysts of a wild *Eimeria* species and collecting the very first parasite that are excreted as a result of infection (J Parasitol. 1975, 61: 1083–1090). However, such attenuated live vaccines produce fewer parasites and give an appreciable disease effect to vaccinated chickens. On the other hand, a protection level using the latter (inactivated vaccine) is far from complete. Furthermore, the disadvantage of these vaccines is expensive to be produced because a large-scale production of these vaccines needs a lot of live chickens.

An alternative solution would be to produce, by genetic engineering, the protective antigens of *Eimeria* parasites. Once developed, these immunogens could be produced cheaply in a prokaryotic or eukaryotic culture system in an unlimited supply and used to vaccinate chickens against coccidiosis.

2. Related Art

Several protective antigen genes of *Eimeria* have been reported. For examples, Jenkins et al. reported screening using a rabbit serum against the membrane fraction of *E. acervulina*, and a part of the cDNA encoding a 250-kDa protein in parasite surface (Exp. Parasitol. 1988; 66: 96–107, U.S. Pat. No. 5,122,471). Some *Eimeria* antigen genes were screened using monoclonal antibodies to Eimeria parasites instead of antisera (U.S. Pat. No. 5,028,694, U.S. Pat. No. 5,279,960, U.S. Pat. No. 5,814,320, U.S. Pat. No. 5,449,768). However, these antigens could elicit only partial protection against Eimeria infection to chickens immunized with a recombinant protein or recombinant virus expressing the antigen (U.S. Pat. No. 5,387,414, U.S. Pat. No. 5,403,581, U.S. Pat. No. 5,602,033, U.S. Pat. No. 6,001,363).

Acquired immune responses are mediated by two different mechanisms, cell-mediated immunity and humoral immunity. The former involves activation of white blood cells such as T-lymphocytes previously sensitized to the immunogen. The latter involves the production of antibodies by lymphoid tissue. Almost all of antigens described above could induce humoral immunity because they were screened by antibodies. However, it is considered that cell-mediated, especially Th1-type immunity plays more important roles in host immune responses against protozoa and bacteria than humoral immunity.

Interestingly, a glycolytic enzyme, GAPDH protein has been shown to be a putative vaccine candidate against *Schistosoma japonicum* or *Schistosoma mansoni* infection (Infect. Immun. 1993; 61: 4716–4723, Vaccine 1999; 17: 13–18), and B- and T-cell epitopic regions on GAPDH of *S. mansoni* have been determined (Vaccine 2000; 18: 2039–2048). Also, GAPDH has been involved as an important immunogenic molecule in several infectious disease models such as African trypanozomiasis and candidasis (J. Infec. Dis. 1995; 172:845–850, Electophoresis 1999; 20: 1001–1010). Moreover, to identify antigen genes that are involved in T-cell-mediated immune response, a genomic library of *Brucella abortus* has been screened, and the GAPDH has been found as a T- and B-cell reactive protein (J. Med. Microbiol. 2002; 51: 661–671).

Few antigens that involve cell-mediated immunity had been found in *Eimeria* spp, and it is difficult to identify them by screening only using antibodies against *Eimeria* parasites.

Moreover, the cDNA library derived from sporocysts or sporozoites, which were not in vivo but in vitro prepared from oocysts, has been used as a screening material in the past. This is because it is very difficult to select only *Eimeria* cDNA from total cDNA, which were prepared from total mRNA in the intestinal cells of the chicken infected with *Eimeria*. However, it is thought to be difficult but very important to screen an effective antigen gene that could elicit a cell-mediated immunity using a cDNA library prepared from the intestinal cells of the chicken infected with *Eimeria*

SUMMARY OF THE INVENTION

The present invention provides a method to identify antigen genes for cell-mediated immunity, and a novel DNA encoding *Eimeria* GAPDH. A nucleotide sequence of *Eimeria* GAPDH provided by this invention is useful to produce a recombinant *Eimeria* GAPDH protein and/or a recombinant virus, that are useful as the recombinant vaccine for coccidiosis.

DETAILED DESCRIPTION OF THE INVENTION

GAPDH

Glyceroaldehyde-3-phosphate dehydrogenase (GAPDH) of the present invention is derived from *Eimeria*, avian parasite, and does, more specifically, comprise the amino acid sequence of SEQ ID NO.2.

DNA

The DNA of the present invention encodes the aforesaid GAPDH protein, and is originally cDNA prepared from the intestinal cells of chicken infected with *Eimeria maxima* and *acervulina.*

A specific example of a DNA of the prevent invention is that of SEQ ID NO.1. However, the DNA of the present invention is not limited only to that sequence. In accordance with degeneracy of genetic code, it is possible to substitute at least one base of the base sequence of a gene by another kind of base without causing the amino acid sequence of the protein produced from the gene to be changed. Hence, the DNA of the present invention may also have any base sequence that has been changed by substitution in accordance with degeneracy of genetic code. That is, the DNA of the present invention is any DNA that encodes the protein encoded by SEQ ID NO. 1, that is, the protein of SEQ ID NO. 2.

The DNA of the present invention can therefore be an isolated (or purified) molecule containing the entire sequence of SEQ ID NO. 1, or a portion of this sequence, or a homologous sequence, as discussed below. If the DNA sequence of the inventive molecule is considered to comprise SEQ ID NO. 1 when the entire SEQ ID NO. 1 is present; additional nucleotides may also be present. If no additional nucleotides are present, the DNA sequence would be considered to be that of SEQ ID NO. 1.

The DNA is readily modified by substitution, deletion or insertion of nucleotides, thereby resulting in novel DNA sequences encoding the protein or its derivatives. These modified sequences are used to produce mutant polypeptide and to directly express the protein. Methods for saturating a particular DNA sequence with random mutations and also for making specific site directed mutations are known in the art; see e.g. Sambrook et al supra, Chapter 15.

The DNA molecule can comprise a part of the nucleotide sequence of SEQ ID NO. 1, and can comprise a nucleotide sequence having more than 90%, more favorably more than 95%, identity to the nucleotide sequence of SEQ ID NO. 1. In this case, identity is calculated using Basic Local Alignment Search Tool (BLAST).

The DNA of the present invention can be modified, if necessary and desired, into recombinant DNA molecules by adding a suitable linker thereto, to construct recombinant vectors, transformants or recombinant viruses, as will be later described.

These recombinant DNA constructs can have nucleotide sequences that do not exist in nature by "ligation" with other DNA sequences. For example, if a signal sequence for secretion is ligated in frame to DNA encoding a protein, the ligated gene is expressed as a secretory protein; or if a DNA sequence for promoter is ligated to a cording sequence, it can control the transcription of the sequence. Generally "ligation" in genetic engineering means to connect two DNA or RNA molecules contiguously (or in close proximity).

The DNA of the present invention can be connected to the linker by conventional genetic engineering. The linker may be at least one or two more nucleotides that are not naturally connected to the DNA of the present invention, and be appropriately designed depending on the site of a vector or virus DNA to be inserted. Ligation of the linker may be effected by any conventional method so long as the expression of each gene is not inhibited. The DNA may be digested with an appropriate restriction enzyme(s) followed by ligating directly or with interposal of a linker to vector or virus DNA.

Recombinant Vectors

Recombinant vectors of the present invention are recombinant vectors comprising at least the DNA of the present invention defined above, and may be a vector in which a promoter (later described) or a marker gene such as lacZ is inserted together. The vector in which the DNA of the present invention is integrated can be chosen from plasmids, cosmids, phages and such, for example, a plasmid such as pBR322, pBR325, pUC7, pUC8, pUC18, pUC19, pBluescript or pGEM, a cosmids such as pHC79, or a phage such as M13 phage. The vector is digested with an appropriate restriction enzyme(s) and the DNA of the present invention or other necessary DNA is inserted therein by the standard procedure.

Recombinant Virus

A recombinant virus of the present invention contains the DNA of the present invention, and is constructed by inserting the DNA into the region that is not essentially required for growth of the parent virus (the non-essential region) by standard procedures. If necessary and desired, promoters and marker genes may also be inserted into the non-essential region, together with the DNA.

(1) Parent Virus

The parent virus in the present invention is a virus used for insertion of the DNA of the present invention into the virus genome. The kind of the virus is not particularly limited as long as it is usable as a virus for the recombinant techniques. Specific examples of the viruses include a herpes virus such as herpes virus of turkey (HVT), Marek's disease virus, infectious laryngotracheitis virus, etc; a pox virus such as fowlpox virus, canary pox, vaccinia virus, etc. Taking their use as the poultry vaccine into consideration, the Marek's disease vaccine strains such as HVT FC126 (serotype 3), SB1 (serotype 2) or Rispens (serotype 1) is particularly suitable for the purpose of the present invention. These viruses are commercially available and thus readily available.

(2) Non-Essential Region

The non-essential region used in the present invention is the genome region non-essential for amplification of the parent virus described above.

There are several reports of the non-essential region of the herpesvirus. For instance, the UL43 gene described in WO 89/01040, the US2 gene in WO 93/25665 and the inter-ORF region between UL44 and UL46 in WO 99/18215 can be used for insertion of the foreign gene. Among these, the inter-ORF region between UL44 and UL46 is most suitable in regard of the virus stability.

Specific examples of the non-essential region of the poxvirus include 7.3 kb EcoRI fragment, 5.0 kb EcoRI-Hind III fragment, 4.0 kb BamHI fragment and 5.2 kb Hind III fragment described in U.S. Pat. No. 5,387,519.

(3) Vector Containing the Non-Essential Region

The vector containing the non-essential region that can be used in the present invention to construct a recombinant virus can be the same as the recombinant vector described hereinbefore. After these vectors are digested with an appropriate restriction enzyme(s), the non-essential region is inserted into the vector by the standard procedure.

(4) Foreign Gene

One of the foreign genes which are incorporated into the viral genome is the GAPDH gene of the present invention in any event. Besides that, genes coding for other antigenic proteins of the genus *Eimeria* or fragments thereof; genes coding for HN, F, etc. of Newcastle disease virus (NDV), or fragments thereof, genes coding for ILTV gB or fragments thereof, or genes coding for MDV gB, gC, gD, etc. or fragments thereof, can also be incorporated in combination as a foreign gene. The foreign gene can be incorporated into one non-essential region of the viral genome, or alternatively, multiple foreign genes may be incorporated into one or multiple non-essential regions of the viral genome.

(5) Homology Vector (Vector for Construction of the Recombinant Virus)

The homology vector of the present invention is one of the recombinant vectors described hereinbefore and can be obtained by inserting at least GAPDH gene of the present invention together with the promoter described hereinafter into the non-essential region of the vector hereinbefore by the standard procedure. In addition to GAPDH gene, other foreign gene hereinbefore or a marker gene such as a lacZ gene may be inserted into the vector for construction of recombinant virus.

(6) Promoter

The promoter used in the present invention is not particularly limited as far as it functions as a promoter in a host cells infected with the recombinant virus. Specific examples of the promoter include a chicken β-actin promoter and an immediate early promoter of cytomegarovirus for recombinant herpesvirus; a 7.5-kDa or 11-kDa polypeptide promoter of vaccinia virus for recombinant poxvirus; etc. These promoters may be modified by partial deletion, etc., so long as they can function as promoters. Synthetic promoters may also be used for the present invention, with reference to B. Moss et al., J. Mol. biol., 210: 749–769, 771–784 (1989).

(7) Construction of Recombinant Virus

Any conventional method can be used for construction of the recombinant virus and there is no particular limitation thereto. For example, the homology vector is transfected into cells previously infected with parent virus or co-transfected into cells with infectious viral genome. Transfection is performed by any known method such as electroporation. The transfected cells are inoculated into culture plates and incubated to cause homologous recombination between the homology vector and the viral genome in the infected cells till the virus plaques become visible. The identifiable plaques include recombinant viruses as well as parent viruses. The recombinant virus is purified from these plaques by any known method. For instance, cells having plaques are diluted to an appropriate concentration, transferred to the 96-well plates and recombinant plaques can be selected by antigen-antibody reaction using the antibody against the *Eimeria* GAPDH as the primary antibody, or by plaque hybridization using the GAPDH gene as a probe. In the case of recombinant virus containing a marker gene such as lacZ, recombinant virus can be more easily selected by forming a blue plaque in the presence of Bluo-Gal (GIBCO-BRL, Inc.), which is one of the substrates for β-galactosidase.

Host cells are not particularly limited so long as the used virus can infect into and propagate in these cells. In the case of herpesvirus such as herpes virus of turkey, chick embryonic fibroblasts (CEF) or duck embryonic fibroblasts can be used, and CEF or embrionated egg chorioallantoic membrane cells can be used in the case of poxvirus Recombinant GAPDH Protein A recombinant GAPDH protein of the present invention is a GAPDH protein produced in microorganisms or cells transformed with at least the DNA of the present invention or with a recombinant vector having the DNA of the present invention for expression. That is, the term "recombinant" here refers to the fact that the DNA expressing the GAPDH protein is used to transform the cells used for expression. The amino acid sequence of the recombinant GAPDH protein is not limited only to that shown in SEQ ID NO.2, but those in which the amino acids are artificially modified by substitution, deletion, addition or insertion, so long as an epitope in the recombinant GAPDH protein is kept. Because any epitope of *Eimeria* GAPDH protein is not known at present, the keeping of the epitope in the recombinant GAPDH protein will be judged by whether chickens immunized with the recombinant GAPDH protein could induce cell-mediated or humoral immunity against *Eimeria* GAPDH protein or not. One example is a recombinant GAPDH protein comprising of the eighth to 339th amino acid sequence of SEQ ID. NO.2 as described in EXAMPLE 5.

The vector to construct the expression vector for the recombinant GAPDH protein is not limited, and may be chosen from the aforesaid vectors for the recombinant vector. The vector to express the objective protein as a fusion protein with a Tag, by which the objective protein could be affinity-purified, is more suitable. For examples of such a vector, PGEX vector (AMERSHAM BIOSCIENCES Corp.) or pQE vector (QIAGEN Inc.) is commercially available. The expression vector for recombinant GAPDH protein can be constructed by well-known techniques in this field.

Using the resulting expression vector for recombinant GAPDH protein, a variety of host cells can be appropriately transformed to obtain a microorganism or cells capable of producing the recombinant GAPDH protein of SEQ ID NO.2 or recombinant GAPDH fusion protein comprising a part of SEQ ID No.2 and a Tag sequence.

Host cells used in herein can be chosen in terms of compatibility of the expression vector, suitability of the products, etc. and may be either prokaryotic or eukaryotic cells. Specific examples of the host cells include bacteria such as the genus *Escherichia* (e.g., *E. coli* ) or the genus *Salmonella* (e.g., *Salmonella typhimurium*), yeast, insect cells, Chinese hamster ovary (CHO) cells, CEF cells, etc.

The host cells transformed by transfection of an appropriate expression vector can be cultured and proliferated under incubation conditions well known to one skilled in the art. For example, the transformed *E. coli* can be well grown in LB medium at 37° C. under aerobic conditions. In producing recombinant GAPDH protein, the condition for the induction of the recombinant GAPDH protein can be chosen according to the used promoter. In the case of *E. coli* lactose promoter and operator system, as a specific example, it is achieved by adding an appropriate amount of isopropyl-1-thio-β-D-galactopyranoside (IPTG) to a culture medium.

A method to purify recombinant GAPDH protein is not particularly limited, but any known method is applicable to the purification in combination with techniques well known in this field. When recombinant GAPDH protein is expressed as a fusion protein containing some Tag that can be used in purification through an affinity column, the affinity column is a very convenient tool. For example, recombinant GAPDH protein expressed as fusion with glutathione S-transferase (GST) could be purified easily through Glutathione Sepharose 4B column (AMERSHAM BIOSCIENCES Corp).

Recombinant Vaccine for Coccidiosis

A recombinant vaccine for coccidiosis of the present invention is a usage of a recombinant virus or recombinant GAPDH protein of the present invention, and consists mainly of the recombinant virus or recombinant GAPDH protein of the present invention. So long as the recombinant vaccine for coccidiosis can be safely immunized to chickens, the vaccine may contain any ingredients such as saline, adjuvant, and/or preservatives.

The administration method of the recombinant vaccines of the present invention is not particularly limited as far as it can induce immune responses to the administered chicken. For example, the recombinant virus is suspended in the phosphate buffer saline (PBS) to give $10–10^5$ PFU/dose, or more favorably $10^{2–104}$ PFU/dose, and inoculated into napes of one day of age chickens subcutaneously or into embryonated eggs by syringe or by any apparatus for injection.

It is preferable that recombinant GAPDH protein is injected with adjuvant, because it can induce strong immune responses to the injected chicken. Adjuvant can be selected among numerous ones well known in this art. For example, oil adjuvant, aluminum hydroxide, or CpG oligonucleotide, which is recognized by toll-like receptor 9 on the cell surface and can activate cell-mediated immunity.

The amount of the injecting recombinant protein is not also limited. For example, recombinant protein of more than 0.1 mg/ml suspended with PBS is well mixed with equal volume of Freund's incomplete adjuvant, and the mixture of 0.2 ml can be injected subcutaneously into the chicken of 4 weeks old. In this case, the booster immunization is preferable, and booster of two times at intervals of a week is more preferable.

BRIEF DESCRIPTION OF THE DRAWING FIGURES

Figure 2:
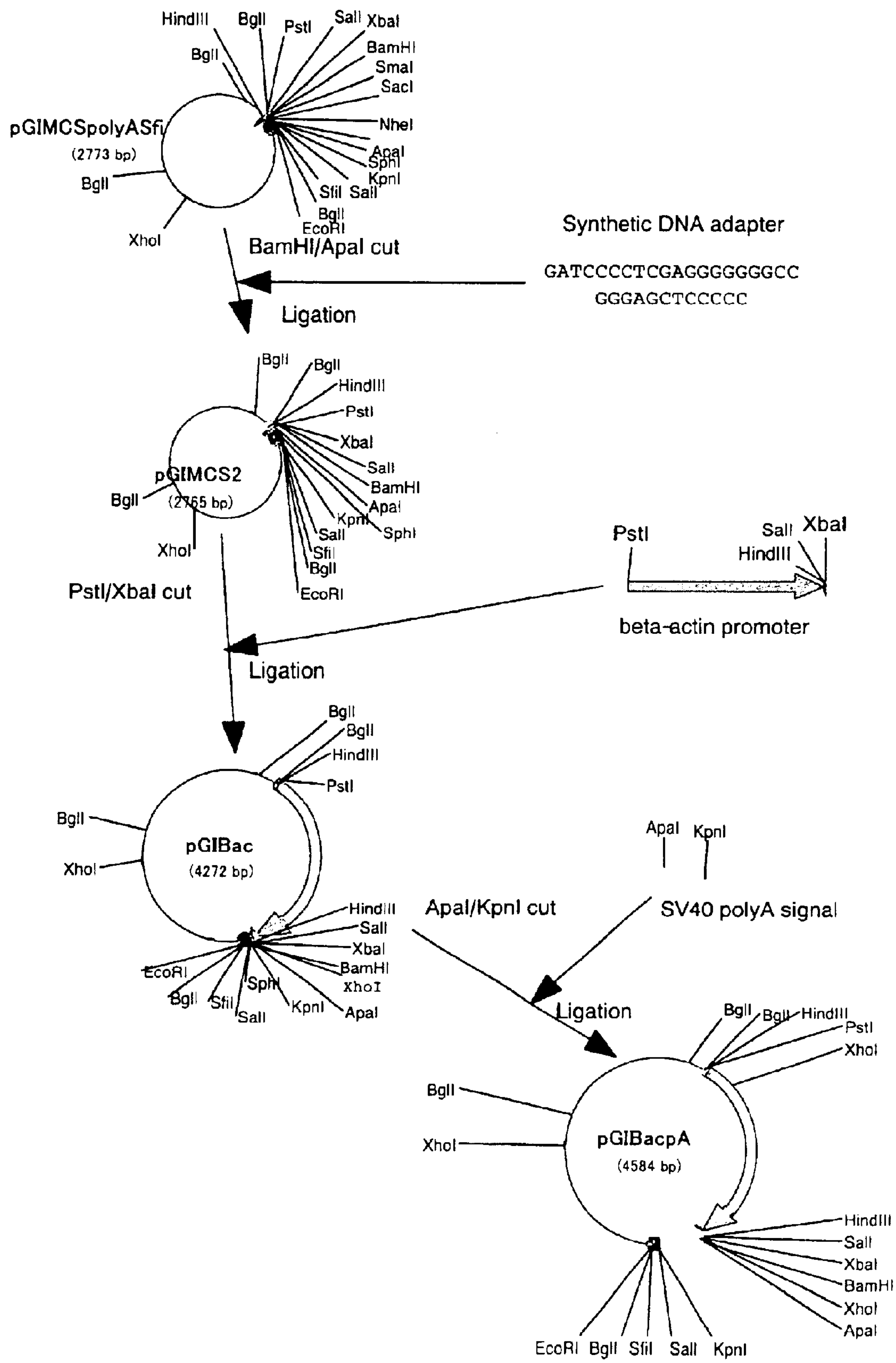
Figure 3:
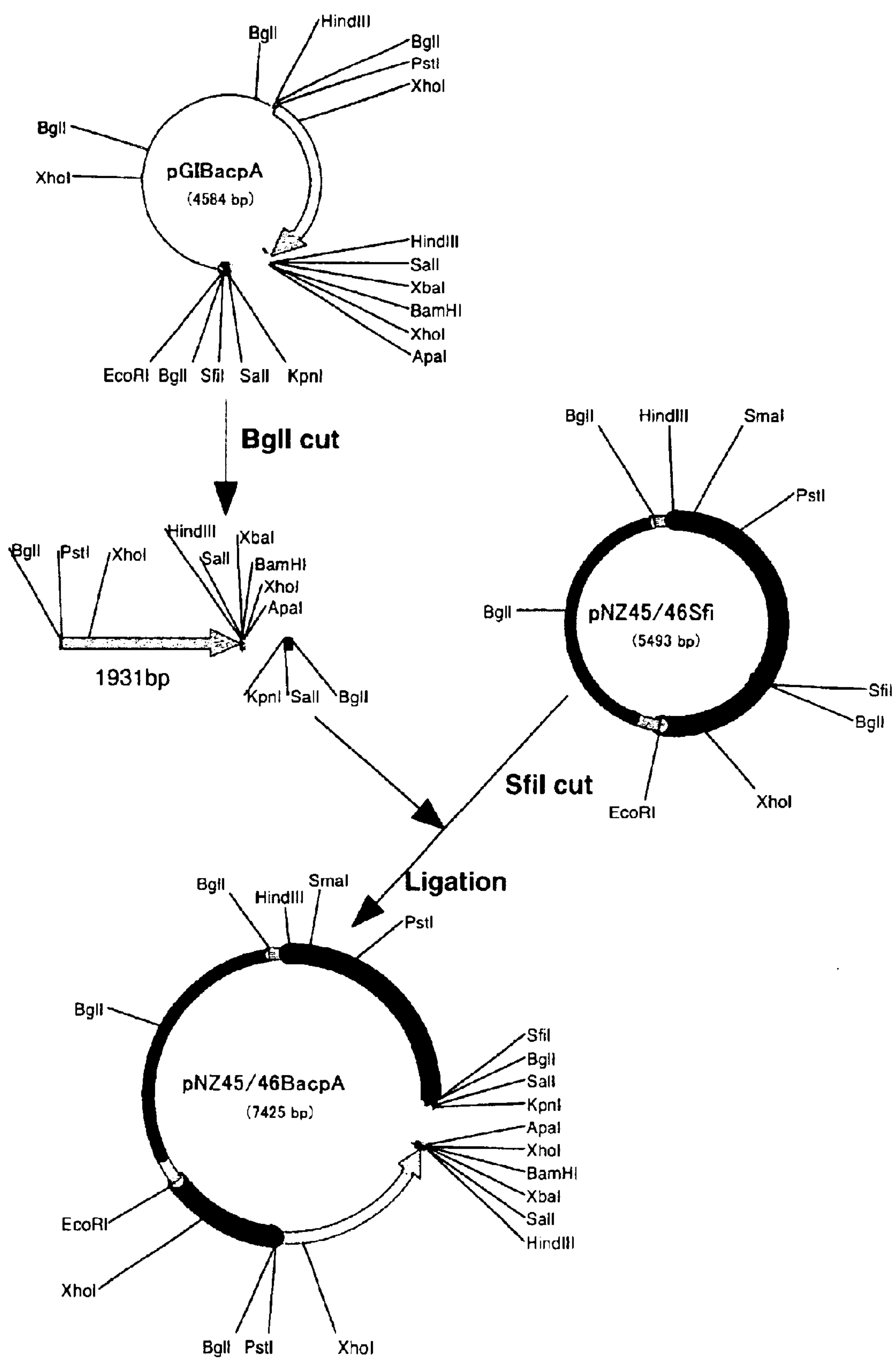
Figure 4:
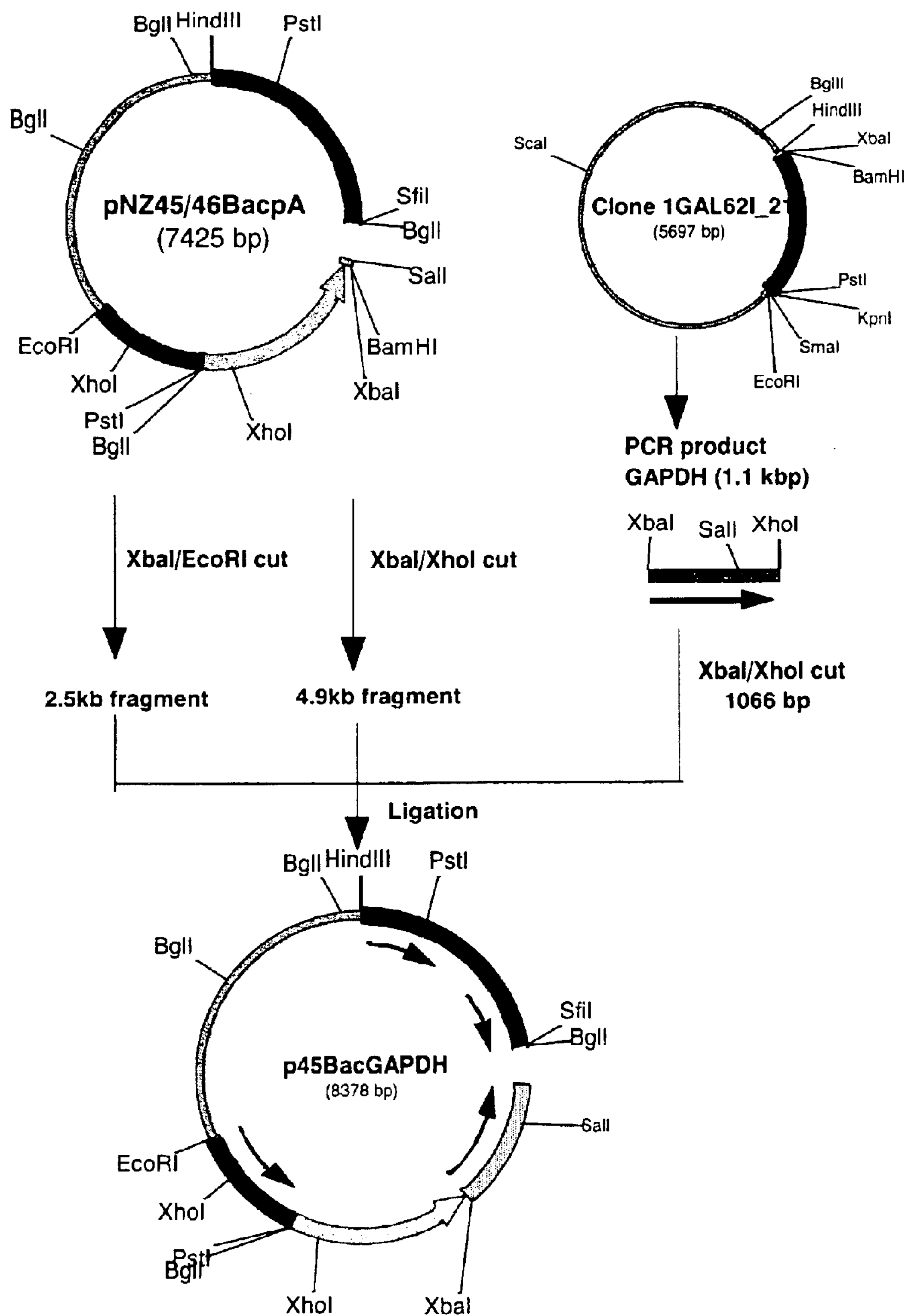
Figure 5:
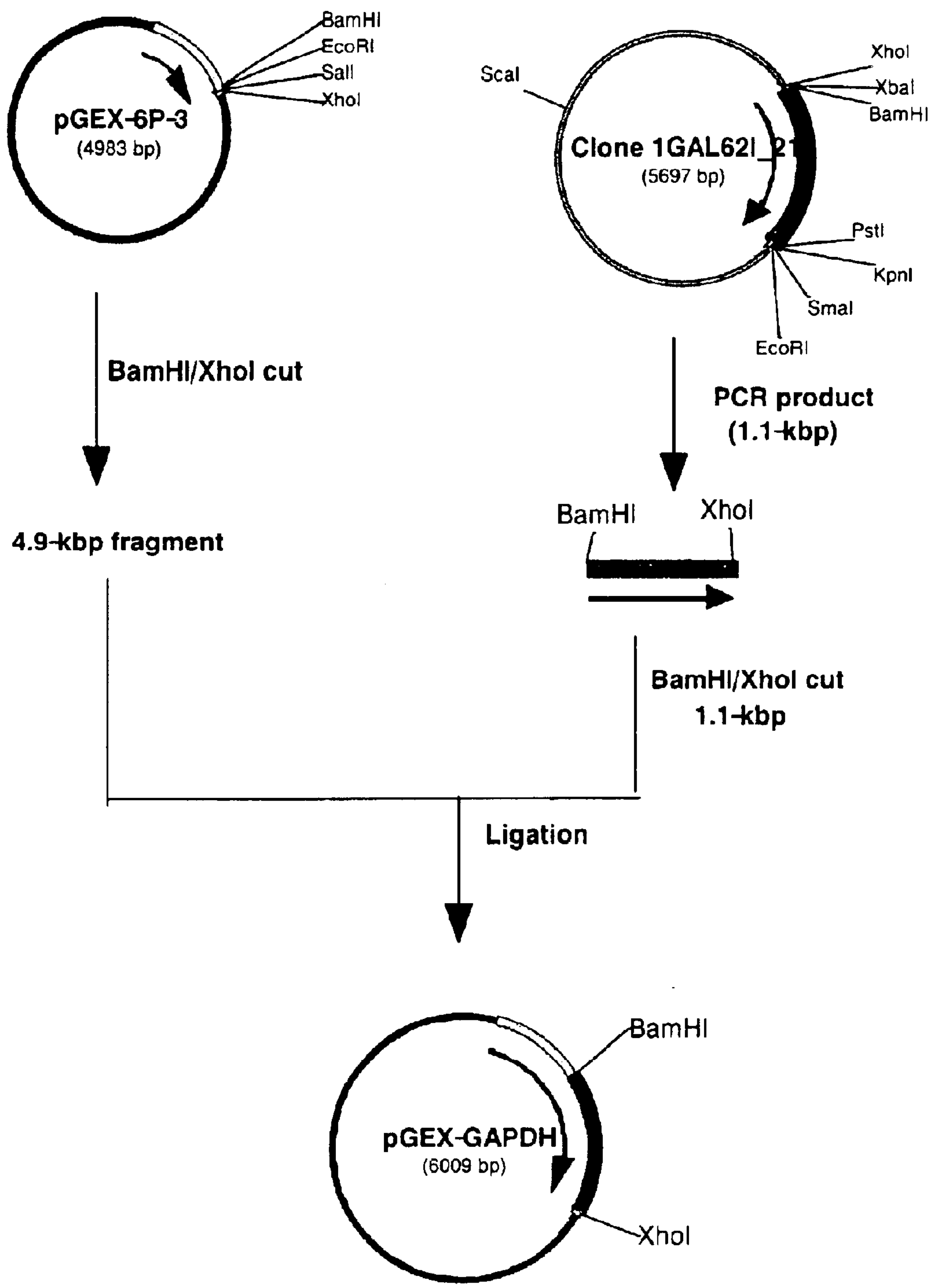

FIG. 1 Effect of the vaccination with the recombinant vector containing *Eimeria* GAPDH gene FIG. 2 Construction of the plasmid pGIBacpA FIG. 3 Construction of the plasmid pNZ45/46BacpA FIG. 4 Construction of the plasmid p45BacGAPDH FIG. 5 Construction of the plasmid pGEX-GAPDH

LIST OF THE SEQ ID SEQUENCES

SEQ ID NO. 1: cDNA Sequence of the GAPDH gene derived from *Eimeria acervulina* or *maxima*.

SEQ ID NO. 2: Amino acid sequence of *Eimeria* GAPDH

SEQ ID NO. 3: Sequence of the chick beta-actin promoter gene

SEQ ID NO. 4: Primer PrBac1

SEQ ID NO. 5: Primer PrBac2

SEQ ID NO. 6: Oligonucleotide Ad-B-A-U

SEQ ID NO. 7: Oligonucleotide Ad-B-A-L

SEQ ID NO. 8: Primer PolyA-F

SEQ ID NO. 9: Primer PolyA-R

SEQ ID NO. 10: Primer XbaGAPDH

SEQ ID NO. 11: Primer GAPDHXho

SEQ ID NO. 12: Primer GAPDHBamH1

SEQ ID NO. 13: Primer GAPDHXhoend

SEQ ID NO. 14: Oligonucleotide CpG

DESCRIPTION OF THE PREFERRED EMBODIMENTS

The plasmid construction was essentially performed by the standard molecular biology techniques (Molecular Cloning: A Laboratory Manual. 2nd Edition, Cold Spring Harbor Laboratory, Cold Spring Harbor, N.Y. 1989). DNA restriction fragments were electrophoresed on agarose gels and purified with QIAquick Gel Extraction Kit (QIAGEN, Cat # 28704).

HVT FC126 strain (Witter R. L. et al. Am. J. Vet. Res. 1970, 31, 525–538) was used as a backbone virus to generate the avian recombinant herpesvirus.

EXAMPLE 1

Preparation of a cDNA Library from Chicken Intestines Infected with *Eimeria*

SC chickens was purchased from Hyline International Production Center (Dallas Center, IA), and hatched at Parasite Biology, Epidemiology and Systematics Laboratory facilities (Beltsville, Md.).

Chickens were given feed and water and provided with constant light. The wild-type strain of *E. maxima* and *E. acervulina* developed and maintained at the Animal and Natural Resources Institute was cleaned by flotation on 5.25% sodium hypochloride, washed 3 times with distilled water and used to infect chickens. Chickens in the experimental group (n=5) were orally infected at 3 weeks of age with $1\times10^4$ sporulated oocysts. Secondary infection was given orally at 9 weeks of age with $2\times10^4$ sporulated oocysts of the homologous parasite.

To get mRNA from intestinal intraepithelial lymphocytes (IELs), IELs were collected from the duodenal region (for *E. acervulina*) or the section from Meckel's diverticulum to the ileac region (for *E. maxima*) at 4 days following primary and secondary infections as described previously (Min et al., 2001). The collected region of the intestine was excised, cut longitudinally, and washed in several changes of ice-cold $Ca^{2+}$ and $Mg^{2+}$-free Hanks' balanced salt solution (CMF-HBSS) containing 10 mM dithiothreitol (DTT). The intestines were cut into 3 cm pieces, incubated with swirling in 250 ml of CMF-HBSS for 10 min at 37° C., and the supernatants were discarded. Intestinal pieces were resuspended two times in 200 ml of CMF-HBSS containing 0.1 mM ethylenediamine tetra-acetic acid (EDTA) and 5% Fetal Calf Serum (FCS), and incubated with swirling for 20 min at 37° C. Cells in the supernatant were passed through nylon wool (Robbins Scientific) to remove dead cells and cell aggregates, and washed with CMF-HBSS. The cells were purified on a discontinuous percoll density gradient by centrifugation at 600 g for 25 min at 24° C. The cells accumulating at the 40/50% interface were collected, washed three times with CMF-HBSS and stored at −80° C.

Total RNAs, first, were extracted from IELs collected from chicken intestines infected with *E. maxima* and *E. acervulina* using TRIzol Reagent (Life Technologies, Gaithersburg, Md.), followed by DNase treatment to remove any DNA carried through the procedure. The mRNA isolation with total RNAs was done using the PolyA Tract mRNA Isolation System IV (Promega, Madison, Wis.) and the concentration and purity of the eluted mRNA were determined by spectrophotometry (Beckman) or through 1% of denaturing agarose gel made using NorthernMax-Gly Kit (Ambion).

Aliquots of the mRNAs prepared from different time points from IELs from chickens which received primary and challenge infections were pooled for constructing a library. A cDNA library was produced using the Superscript Plasmid System (Life Technologies) for cDNA synthesis and plasmid cloning. The cDNA was directionally cloned into NotI-SalI region of the eukaryotic expression vector pCMV-SPORT6 (Life Technologies) according to manufacturer's recommendations. The cDNA library was transformed into electroMAX DH10B competent cells (Life Technologies) and amplified once using LB plates containing ampicillin to preserve the distribution of clones in original library. The cDNA library was stored at −80° C.

EXAMPLE 2

Screening of a cDNA Clone Encoding *Eimeria* GAPDH

Normalization of cDNA Libraries

Discovery of novel gene sequences was greatly facilitated by using normalized cDNA libraries. Somatic cell mRNAs were distributed into three classes; namely, prevalent, intermediate, and rare. In the average cell, the most prevalent class of RNA consists of 10 species, each of which was present at about 5,000 copies per cell. In contrast, the least abundant class contains approximately 15,000 different mRNAs, each of which is present at 1–15 copies per cell.

Method to remove prevalent RNA is based on colony hybridization. A cDNA library was spread on solid media and the colonies were transferred to nylon membranes. The membranes were hybridized with [$^{32}$P]-labeled prevalent RNA. The negative colonies were selected for sequencing and analysis.

Method to normalize cDNA library was based on reassociation kinetics. When a population of DNA molecules is denatured, the rate of reassociation is second-order with respect to the concentration of single-stranded DNA. Therefore, rare species anneal more slowly and as the reassociation reaction proceeds, the remaining single-stranded DNA becomes increasingly normalized.

Library Characterization

Clone inserts were amplified by PCR using isolated plasmid as template with T7 and SP6 vector primers. The amplified inserts were precipitated with isopropanol to remove protein and unreacted primers and resuspended in TE buffer (pH 8.0). Sizes of inserts were determined by agarose gel electrophoresis. PCR amplified inserts were spotted to nylon filters using a BioMek 2000 robot (Beckman Coulter, Inc.) and hybridized with [$^{32}$P]-labeled genomic DNA from chicken, *E. maxima* and *E. acervulina* to identify clones representing chicken and *Eimeria*, respectively.

Sequencing

Colonies were plated and about 5,000 colonies were picked. Each colony was placed into each well of microtiter plates and cultured at 30° C. for 16 hours. Preparation of plasmid DNA from a cDNA library was carried out using the Qiagen miniprep kit. DNA concentration was determined by optical density at 260 nm (Beckman) and adjusted to approximately 1 mg/ml. The DNA was aliquoted and stored at −80° C. for sequencing.

In case of the automated sequencing, template DNA and T7 primers were added to the PCR mixture including Tag DNA polymerase, buffer, nucleotides, and fluorescent-labeled dye terminators. PCR reactions were subjected to the initial denaturation at 94° C. for 5 min and processed through 25 temperature cycles consisting of denaturation at 94° C. for 1 minute, annealing at 55° C. for 1 minute, and extention at 60° C. for 1 minute. The reaction mixtures were precipitated by addition of 70% isopropanol with mixing, and centrifugation at 3200 rpm for 30 minutes at room temperature. Residual isopropanol was removed by inverting the 96-well plate and centrifuging at 600 rpm for 2 minutes. Pellets were washed with 70% ethanol and residual ethanol was removed as above. The plate was air dried for 5 to 10 minutes and stored in a desiccator at −20° C. Immediately prior to placing the mixture in the loading chamber of the sequencer, 30 $\mu$l of ultra pure formamide was added and the tube was spin at 2000 RPM for 3 minutes at room temperature (RT). The samples were run on capillary electrophoresis-based automated sequencing system from Applied Biosystms, the ABI 3700 (BARC3700 facility). After data collection, sequence data were created by the ABI software which related the fluorescent signal and viewed as either a four-color raw fluorescent signal or a string of nucleotides.

Sequence Analysis

Similarities to the edited sequences were searched against the National Center for Biotechnology Information (NCBI) non-redundant necleotide and protein databases using BLASTn and BLASTx, respectively. Matches with a P value of $10^5$ or less were considered to be significant. The sequence data were annotated and submitted to GenBank. Redundancy was determined by comparing the ESTs against each other with BLASTn.

EXAMPLE 3

Identify a cDNA Clone Encoding *Eimeria* GAPDH

From the above analyses of about 5,000 clones, EST sequence of a clone (designated as 1GAL62I_21) was found to have the highest similarity to EtESTee33e09.yl (GeneBank Acc: BM306616) that is one in *E. tenella* EST library by BLASTn search, and to *Toxoplasma gondii* (*T. gondii*) GAPDH genes (GeneBank Acc: AAK20420) by BLASTx search.

Then, insert cDNA of clone 1GAL62I_21 was sequenced completely, and found to be 1,280 bp containing a polyA stretch at its 3' end, which is shown in SEQ ID NO. 1. In this cDNA, there is one open reading frame (ORF) of 339amino acids, which is shown in SEQ ID NO. 2.

The amino acids sequence of SEQ ID NO.2 was found to have 76% (259/339 amino acids) identity and 88% (298/339 amino acids) similarity to that of *T. gondii* GAPDH of 340 amino acids by NCBI BLASTp search. The second highly homologous protein was *P. falciparum* GAPDH (GeneBank Acc: NP_702487) and had 71% homology to that of SEQ ID NO.2. Because other known GAPDH proteins of many organisms were listed as homologous proteins by BLASTp search, this clone was thought to be *Eimeria* GAPDH gene. Complete amino acid or nucleotide sequence of *Eimeria* GAPDH has not been reported at the present time, and this patent is the first report about it.

EXAMPLE 4

Effects of Chickens Injected with the Recombinant Vector Containing *Eimeria* GAPDH Gene Fertilized SPF eggs were purchased from SPAFAS, and hatched. The hatched chickens were divided into three groups (9 birds per group). Plasmid 1GAL62I_21 of 25 or 50 g were diluted in HBSS to 0.1 ml and inoculated twice subcutaneously in the leg muscle of chickens with a gene gun at 1 and 2 weeks of age. Control chickens were inoculated with HBSS medium. Three weeks later, chickens were challenged orally with 10,000 sporulated oocysts of *E. acervulina* Beltsville strain. Fecal oocysts were collected from day 6 to 9 post challenge, and ground in 2-litter water. After floating in sucrose oocysts were counted microscopically using a McMaster chamber. Total oocyst numbers were calculated using the following formula:

Total oocyst number=(oocyst count)×(dilution factor)×(fecal sample volume)/(counting chamber volume)

The average numbers of oocysts from chickens of control, and 25 or 50 $\mu$g injection groups were 386, 260, and 267×10E6, respectively (FIG. 1). These results suggested that GAPDH might be useful antigen.

EXAMPLE 5

Construction of a Homology Vector to Make a Recombinant HVT containing *Eimeria* GAPDH Gene Isolation of the Chick Beta-Actin Promoter Gene Using cellular DNA of CEF cells as a template, amplified 1.5 kb DNA containing the chicken beta-actin promoter was obtained by polymerase chain reaction (PCR). PrBac1 (SEQ ID NO.4) and PrBac2 (SEQ ID NO. 5) were the primer set used for PCR. The obtained DNA was digested with PstI and XbaI and inserted into pUC18. The sequence of the inserted DNA was determined as described before and confirmed to be that of the beta-actin promoter which was 1,525 bp long (SEQ ID NO. 3).

PrBac1 (SEQ ID NO. 4) 5'-CAGTGTCGCTGCAGCTCAGTGCATGCACGCTCATTGCCC-3'

PrBac2 (SEQ ID NO. 5) 5'-GCTCTAGAGTCGACMGCTTGGGGGCTGCGGAGGMCAGAGAGGGMG-3'

Construction of Plasmid pGIBacpA

A DNA adapter consisting of synthetic oligonucleotides Ad-B-A-U (SEQ ID NO. 6) and Ad-B-A-L (SEQ ID NO. 7) was inserted between BamHI and ApaI sites of pGIMC-SpolyASfi (2,773 bp, WO 99/18215) to generate plasmid pGIMCS2 (2,765 bp).

```
DNA adapter
5'-GATCCCCTCGAGGGGGGGCC-3'

     3'-GGGAGCTCCCCC-5'
```

Plasmid pGIMCS2 was then digested with PstI and XbaI and ligated with the beta-actin promoter described above to give plasmid pGIBac (4,272 bp).

Next, using pBK-CMV (STRATAGENE, Cat. #212209) as a template and PolyA-F (SEQ ID NO. 8) and PolyA-R (SEQ ID NO. 9) as a set of primers, DNA including SV40 polyA signal was amplified by PCR. Digestion of the amplified DNA with ApaI and KpnI gave a 334 bp SV40 polyA signal DNA.

The DNA was then inserted into pGIBac, which had been digested with ApaI and KpnI, to generate pGIBacpA (4,584 bp, FIG. 1).

```
PolyA-F
5'-GCGGGCCCTAATTGTTTGTGTATTTTAG-3'   (SEQ ID NO. 8)

PolyA-R
5'-TTGGTACCGCTTACAATTTACGCGTTAAG-3'  (SEQ ID NO. 9)
```

Construction of Plasmid pNZ45/46BacpA (FIG. 2)

Plasmid pGIBacpA was digested with BglI, electrophoresed on agarose gels and 1,931 bp DNA fragment was recovered from the gels. The recovered fragment was then ligated to plasmid pNZ45/46Sfi (5,493 bp, WO 99/18215), which had previously been digested with SfiI, to obtain pNZ45/46BacpA (7,425 bp).

Construction of Plasmid p45BacGAPDH (FIG. 3)

To introduce two restriction enzyme sites (XbaI and XhoI sites) before and behind the ORF coding GAPDH, PCR was carry out using clone 1GAL621_21 as a template, and XbaGAPDH (SEQ ID NO. 10) and GAPDHXho (SEQ ID NO. 11) as a set of primers.

The amplified 1.1-kbp PCR products were digested with XbaI and XhoI, and the resultant 1,066 bp fragment was ligated with 2.5-kbp XbaI-EcoRI and 4.9-kbp EcoRI-XhoI fragments, both of which were excised from pNZ45/46BacpA, to generate p45BacGAPDH (8,378 bp, FIG. 3), which was used as a homology vector to make recombinant HVT.

```
XbaGAPDH
5'-CCTTACTCAGTCTAGAAAATGGTGTGCCG-3'  (SEQ ID NO.10)

GAPDHXho
5'-CTAAAGTGTACTCGAGTAAGGCGACAG-3'    (SEQ ID NO.11)
```

EXAMPLE 6

Production of Recombinant GAPDH Protein

Construction of an *E. coli* Expression Vector for *Eimeria* GAPDH

To express and purify a recombinant GAPDH protein as a GST fusion protein, an *E. coli* expression vector pGEX-GAPDH was constructed as follows (FIG. 4). To ligate GAPDH DNA into a pGEX-6p-3 vector (AMERSHAM #27-4599-01) containing GST gene, DNA fragment of about 1.1-kbp introducing restriction enzyme sites (BamHI and XhoI sites) in the ORF of GAPDH was amplified by PCR using clone 1GAL62I_21 as a template, and GAPDH-BamH1 (SEQ ID NO. 12) and GAPDHXhoend (SEQ ID NO. 13) as a set of primers. The amplified DNA fragment of about 1.1-kbp was cut with BamHI and XhoI, fractionated by an agarose gel electrophoresis, and purified with QIAquick Gel Extraction Kit (QIAGEN K.K., Japan; #28704). Plasmid pGEX-6p-3 was also cut with BamHI and XboI, fractionated by an agarose gel electrophoresis, and purified with QIAquick Gel Extraction Kit. These recovered DNA fragments were ligated to generate pGEX-GAPDH, and transferred into competent *E. coli* cells of JM109 (TaKaRa Bio Inc., Japan). The resulting ampicillin-resistant transformants were randomly picked up and cultured with each 2-ml LB broth containing ampicillin (LB+amp). Each plasmid was prepared by the standard (alkaline lysis) methods, and analyzed by restriction enzyme cutting. An objective plasmid selected by restriction enzyme analysis was sequenced with two sequence primers of AMERSHAM #27-1410-01 and 27-1411-01 to confirm that GAPDH gene was inserted in frame into the pGEX vector.

```
GAPDHBamH1:
5'-GTGCCGTATGGGATCCAACGGCTTCGG-3'(SEQ ID NO. 12)

GAPDHXhoend:
5'-CTAAAGTGTACTCGAGTAAGGCGACAG-3'(SEQ ID NO. 13)
```

Expression of Recombinant GAPDH Protein

*E. coli*BL21 cells (AMERSHAM #27-1542-01) were transformed with the pGEX-GAPDH. The resulting transformants were cultured with LB+amp broth for 16 hours, inoculated into fresh 100 volumes of LB+amp broth and continues to be culture for two hours. They were cultured for more three hours after adding IPTG to a final concentration of 1 mM, harvested by centrifugation, and lysed with Laemmli sample buffer (60 mM Tris-Cl (pH6.8), 25% glycerol, 2% SDS, 5% 2-mercaptoethanol, 0.01% bromphenol blue) by boiling at 100° C. The lysate was applied to 12.5% SDS-polyacrylamide gel electrophoresis (PAGE), and the gel was stained with 0.05% Coomassie brilliant blue (CBB) solution.

The expected protein of about 62-kDa was induced very well as a GST-fusion protein.

Purification of Recombinant GAPDH Protein

BL21 cells transformed with pGEX-GAPDH were cultured in a 2-ml LB+amp broth for 16 hours, and inoculated into fresh 100-ml LB+amp broth and continued culture for two hours. They were cultured for more three hours after adding IPTG to a final concentration of 1 mM, harvested and wash with Phosphate buffer saline (PBS) twice. The cell pellet was suspended with Lysis buffer (50 mM Tris-Cl (pH8.0), 150 mM NaCl, 1 mM EDTA, 0.2 mM 4-(2-aminoetyl)-benzenesulfonyl fluoride hydrochloride (Merck Ltd., Japan; product Name: Pefabloc SC), 1.5 mg/ml lysozyme), and shaken slowly for one hour and more 20 minutes followed by adding Triton X-100 to a final concentration of 0.3%. The suspension was transferred to a tube and centrifuged at 12,000×g for 30 minutes. The pellet and supernatant were separated and applied to 12.5% SDS-PAGE. Most of fusion proteins were found in the pellet fraction.

The pellet was suspended with Laemmli sample buffer, boiled and applied to 8% SDS-PAGE. The objective fusion protein of 62-kDa was eluted and fractionated from the gel region in which the protein existed using Mini Whole Gel Eluter (Bio-Rad) with the elution buffer (60 mM Tris-Cl (pH 8.7), 25 mM boric acid). Recovered proteins in the fractions were checked by a 12.5% SDS-PAGE and CBB staining, and the fraction in which the objective protein existed and other proteins were not contaminated was selected. The recombinant GAPDH protein of 62-kDa of about 1 mg was purified from BL21 transformants cultivated with LB+amp broth of 100 ml as described herein.

EXAMPLE 7

Immune Response of Chickens Vaccinated with Recombinant GAPDH Protein

Recombinant GAPDH protein (0.2 mg) purified as described in the above Example 5 was mixed with 15 $\mu$g of synthetic oligonucleotide CpG (SEQ ID NO. 14) and with equal volume of Freund's complete adjuvant (FCA; Sigma) to form 2 ml micelles. Ten chickens of 4 weeks old were subcutaneously immunized (sc) with each of 0.2 ml micelles, and boosted sc two times at intervals of a week with the same amount of recombinant GAPDH protein and CpG plus incomplete Freund's adjuvant (IFA; Sigma).

CpG (SEQ ID NO. 14): 5'-TCCATGACGTTCCTGACGT-3'

Ten days later after the last immunization, the immunized chickens were bled for about 2 ml each, and the peripheral blood lymphocytes and sera were prepared by the standard techniques. From five non-immunized chickens, the peripheral blood lymphocytes and sera were also prepared as negative control samples.

The antibody in the sera against *E. acervulina* sporozoites was checked by western blotting method. *E. acervulina* of $1\times10^7$ sporozoites were lysed with Laemmli sample buffer and boiled for 5 min, and applied to 12.5% SDS-PAGE. After PAGE, proteins of sporozoites were blotted to a PVDF membrane (MILLIPORE; product name: Immobilon). After blotting, the membrane was dried and cut into total 12 pieces. Each piece was incubated with each serum (1:500 dilution) for 1 hour at RT. After washing with PBS twice, the membrane was incubated with Goat anti-Chicken IgG (H+L) alkaline phosphatase conjugated (1:1,000 dilution; Bethyl, Inc. Catalog #A30-106AP) for 1 hour at RT, washed with PBS several times, and developed with the substrate solution of bromochloroindolyl phosphate/nitro blue tetrazolium (BCIP/NBT). All of 10 sera prepared from immunized chickens reacted specifically to 36-kDa protein of sporozoites, while two negative control sera did not, although there were some proteins reacted nonspecifically. These results indicated that the recombinant GAPDH protein could induce humoral immunity to chickens.

It is checked by T cell proliferation assay whether recombinant GAPDH protein can induce cell-mediated immunity or not. The prepared peripheral blood lymphocytes are suspended with RPMI1640 medium (Sigma), 10% (v/v) fetal calf serum (FCS), 2 mM L-glutamine, 100 U penicillin/ml, 100 $\mu$g streptomycin/ml, and $2\times10^{-6}$ M 2-mercaptoethanol, to a cell density of approximately $1\times10^7$ cells/ml, and 0.1 ml each are transferred into 96-well flat-bottom plates. After the plates are incubated at 41° C. in 5% $CO_2$ for 16 hours, 10 $\mu$l antigen solutions are added into each well of the half. *E. acervulina* sporozoites of $5\times10^5$, $1\times10^6$, or $3\times10^6$ suspended in PBS are sonicated and used as antigen solution. Plates with or without antigen are incubated for more 64 hours at 41° C. in 5% $CO_2$.

At the end of 64 hours, 0.5 $\mu$Ci of (3H) thymidine (specific activity, 6.6 Ci/mmol; NEN) are added to each well, and the plates are incubated under the same conditions for an additional 18 hours. The cells are then harvested onto glass fiber sheets (MILLIPORE; #APFCO2500). The filters are placed in scintillation fluid, and incorporation of the radioisotope into T cells is determined in a liquid scintillation counter (model LS3801; Beckman Coulter, Inc). Duplicate wells are used for each concentration of antigen tested.

EXAMPLE 8

Isolation and Purification of Recombinant HVT Expressing GAPDH Protein

Viral DNA of HVT FC126 strain (wt-HVT) was prepared as described by Morgan et al. (Avian Diseases, (1990) 34:345–351).

$10^7$ primary CEF cells were suspended in Saline G (0.14 M NaCl, 0.5 mM KCl, 1.1 mM $Na_2HPO_4$, 1.5 mM $NaH_2PO_4$, 0.5 mM $MgCl_2$, 0.011% glucose) and co-transfected with 5 $\mu$g of p45BacGAPDH (described in EXAMPLE 4) and 25 $\mu$g of viral DNA by electroporation. Electroporation was performed on Bio-Rad Gene Pulser. Transfected cells were incubated for 10 min at room temperature and transferred to one well of a 6-well plate, which contained 5 ml medium consisting of Leibovitz's L-15, McCoy's 5A Medium (1:1) and 4% calf serum (LM (+) medium). After incubating at 37° C. for 6 days in 5% $CO_2$, harvested cells were diluted serially in freshly prepared secondary CEF cells, plated to the 96-well plates, and incubated for three more days.

When the plaques became visible, the cells were detached from plates by trypsinization, diluted in freshly prepared secondary CEF cells, transferred equally to two 96-well plates and incubated for 3 days to visualize the plaques. One of two plates was then stained with chicken anti-GAPDH serum (described in EXAMPLE 6) as the primary antibody. After detecting the well containing the stained recombinant plaques, cells from the corresponding well of the other plate were recovered, diluted in fresh secondary CEF cells and transferred equally to two 96-well plates to complete the first round of purification.

The purification procedure was repeated until every obtained plaques were stained positively by anti-GAPDH serum. The purified recombinant HVT was designated rHVT/GAPDH.

EXAMPLE 9

GAPDH Gene Expression by the Recombinant Virus

The rHVT/GAPDH or wild-type HVT was propagated for 72 hours at 37° C. on $1\times10^7$ CEF cells in a 75-$cm^2$ flask to $1\times10^5$ pfu. Cells were recovered by scraping, transferred to a 15 ml Falcon tube and subjected to centrifugation at 2,000 rpm for 5 min. After washing with 10 ml of PBS, harvested cell pellets were suspended with 0.1 ml of Laemmli sample buffer, and boiled. The lysates were applied to 12.5% SDS-polyacrylamide gel electrophoresis (PAGE). After PAGE, proteins on the gel were blotted to a PVDF membrane (MILLIPORE; product name: Immobilon). After blotting, the membrane was dried and incubated with chicken anti-GAPDH serum that was gotten in EXAMPLE 6 (1:200 dilution) for 1 hour at RT. After washing with PBS twice, the membrane was incubated with Goat anti-Chicken IgG (H+L) alkaline phosphatase conjugated (1:1,000 dilution; Bethyl, Inc. Catalog #A30-106AP) for 1 hour at RT, washed with PBS several times, and developed with the substrate solution of BCIP/NBT. The expected protein of about 36-kDa was specifically detected in the lane for rHVT/GAPDH to compare with the lane for wild-type HVT.

We claim:

1. An isolated DNA molecule encoding *Eimeria* glyceroaldehyde-3-phosphate dehydrogenase (GAPDH) of the amino acid sequence shown in SEQ ID NO.2.

2. The DNA molecule as described in claim 1, wherein the sequence of said DNA molecule comprises the nucleotide sequence shown in SEQ ID NO. 1.

3. The DNA molecule of claim 2, wherein the sequence of said DNA molecule consists of the nucleotide sequence shown in SEQ ID NO. 1.

4. A recombinant virus whose sequence comprises the sequence of the DNA molecule of claim 1 or 2.

5. A recombinant vector whose sequence comprises the sequence of the DNA molecule of claim 1 or 2.

6. A recombinant virus as set forth in claim 4 wherein said virus is an avipox virus or a herpes virus.

* * * * *